United States Patent [19]

Ascher

[11] Patent Number: 5,249,962
[45] Date of Patent: Oct. 5, 1993

[54] METHOD AND DEVICE FOR CLEANING THE SURFACES OF ABUTMENT MEMBERS OF DENTAL IMPLANTS ESPECIALLY THE LINGUAL SURFACES

[76] Inventor: Jay Ascher, 422 E. Waukena Ave., Oceanside, N.Y. 11572

[21] Appl. No.: 796,034

[22] Filed: Nov. 20, 1991

[51] Int. Cl.⁵ .................................................. A61C 3/00
[52] U.S. Cl. ...................................................... 433/141
[58] Field of Search ............ 433/141, 142, 143, 144, 433/229; 132/321, 322, 323, 324, 329; 128/62 A; 15/167.1, 167.2

[56] References Cited

U.S. PATENT DOCUMENTS

| | | | |
|---|---|---|---|
| 4,795,344 | 1/1989 | Brewer, Jr. | 433/141 |
| 4,832,063 | 5/1989 | Smole | 132/321 |
| 4,941,227 | 7/1990 | Sussman | 15/167.1 |
| 5,050,625 | 9/1991 | Siekmann | 132/323 |
| 5,067,195 | 11/1991 | Sussman | 15/167.1 |
| 5,094,256 | 3/1992 | Barth | 433/80 |
| 5,123,841 | 6/1992 | Millner | 132/322 |

*Primary Examiner*—Cary E. O'Connor
*Attorney, Agent, or Firm*—Ladas & Parry

[57] ABSTRACT

A method and device for cleaning abutment members of a dental implant in which a relatively rigid support member carries a cleaning element into a position around the lingual surface of the abutment member to be cleaned whereafter the cleaning element can be rubbed against the abutment member to effect the cleaning. The cleaning element can be fixed to the support member in which case, the support member is manipulated to achieve the cleaning of the abutment member by the cleaning element. Alternatively, the support member can be removed from the mouth after the cleaning element has been put into place around the abutment member whereafter cleaning of the abutment member is achieved by the cleaning element itself.

19 Claims, 2 Drawing Sheets

METHOD AND DEVICE FOR CLEANING THE SURFACES OF ABUTMENT MEMBERS OF DENTAL IMPLANTS ESPECIALLY THE LINGUAL SURFACES

FIELD OF THE INVENTION

The invention relates to dental cleaning equipment and associated methods and particularly to a dental cleaning device and method for cleaning the surfaces of abutment members of dental implants especially the lingual surfaces.

BACKGROUND

After a relatively long period of slow development, implants are rapidly gaining popularity as an alternative to removable partial and complete dentures. The implants are more secure and less likely to irritate gums or harm adjacent natural teeth. The current popularity of dental implants is the outgrowth o the discovery that titanium is compatible with bone tissue when used in an implant. The phenomenon of "osseointegration" leads to a permanent anchor of the implant in the bone tissue of the patient.

In order to prevent peri-implant disease, regular maintenance of the implant system is essential. Most scientific evidence indicates that bacterial plaque is a principal pathogenic factor affecting implants. A correlation has been reported between inadequate plaque control and increased bone loss. Hence, sound hygiene measures for implant maintenance require a plaque-free environment around implants, teeth and prostheses.

The lingual surfaces of the abutment members of the implant pose a particular problem as far as plaque removal since they are not readily accessible and in order to clean these lingual surfaces, conventional yarns, floss or gauze must be brought into contact with the lingual surface and rubbed thereon. However, it is difficult to insert the cleaning article from the facial side and cross it around the lingual surface of the abutment member and retrieve the free end of the cleaning article at the opposite surface of the abutment member. This is particularly the case when the implants may be obscured by surrounding tissue or are actually lower than the surrounding tissue, making plaque removal very difficult with conventional materials.

A product is known in which a flat braided ribbon serving as a flossing agent is integrated at one end with a J-shaped member of self-sustaining shape made from a flexible material which is thinner than the ribbon. The J-shaped member serves as a means for guiding the braided ribbon around the lingual surface o an abutment member after which the braided ribbon is crossed over on the facial surface to wrap around the abutment member so that the abutment member can be cleaned by rubbing the ribbon thereon. Cleaning is effected by the ribbon, the J-shaped member serving no purpose after the ribbon is engaged around the abutment member.

SUMMARY OF THE INVENTION

An object of the invention is to provide a dental cleaning device and associated method which will enable a patient to clean the surfaces of abutment members of dental implants, especially the lingual surfaces, with relative ease and effectiveness.

A further object of the invention is to provide such a cleaning device which is relatively inexpensive and which can be comfortably employed in a simple manner at home by a patient.

In accordance with the above and further objects of the invention, the dental cleaning device comprises a support member including a relatively rigid handle carrying an operative portion which is constituted and shaped to penetrate between spaced adjacent abutment members of dental implants and which includes a deviated portion to confront a lingual surface of an abutment member when the operative portion is inserted between two adjacent abutment members. A cleaning means, having a flexibility much greater than that of the support member serves to engage the lingual surface of the confronted abutment member to clean the lingual surface by moving the handle member and the cleaning element therewith on and around the lingual surface with a reciprocating movement.

In further accordance with the invention, the operative portion of the support member is made of a thermoplastic material capable of "squeezing" between the adjacent abutment members, if necessary, when inserted therebetween. According to one embodiment, the deviated portion has a rounded, hook shape for engaging around the lingual surface of the abutment member.

In a particular embodiment, the operative portion is an elongated loop of "C" shape with two opposed rounded portions, one for cleaning the lingual surface of an abutment member and the other for cleaning the facial surface of the abutment member, the straight portion of the "C" serving for cleaning the proximal surfaces of the abutment member.

In yet another embodiment, the operative portion comprises a yoke having opposed arms with a tensioning element joining the arms and when the tensioning element is placed against the facial surface of the abutment member and the yoke is advanced so that the abutment member will enter between the arms, the arms undergo deformation and encircle the lingual surface of the abutment member so that the entire surface of the abutment member can be cleaned by reciprocating or oscillating the yoke on the abutment member.

According to a further embodiment of the invention, a conventional cleaning element in the form of a ribbon or the like extends freely through a "J" shaped support member and is freely slidable therein. The hook part of the "J" member is engaged around the lingual surface of the abutment member to position a free end of the ribbon in extending relation at the facial side of the abutment member. After removing the "J" member from the mouth of the user, the opposite ends of the ribbon are engaged by the user and crisscrossed to rub against the surfaces of the abutment member to clean the same.

According to a feature of the invention, the support member can be connected to a vibratable source in order to achieve a cleaning of the abutment member by vibrating the support member.

According to a further feature of the invention, the support member can be provided with an irrigation channel to which can be attached a source of water under pressure. Cleaning can then be assisted by water irrigation.

According to the method of the invention, a relatively rigid support member is utilized to position a cleaning means at the lingual surface of the abutment member so that the cleaning means can clean the lingual surfaces of the abutment member. The cleaning means can be fixed to the support member in which case it is the support member itself which is oscillated on the surfaces to effect the cleaning of the abutment member. Alternatively, the cleaning means can be slidably carried by the support member into its operative position at the lingual surface of the abutment member after which the support member is removed and cleaning is effected by the cleaning means alone.

DETAILED DESCRIPTION OF PREFERRED EMBODIMENTS

Figure 1:
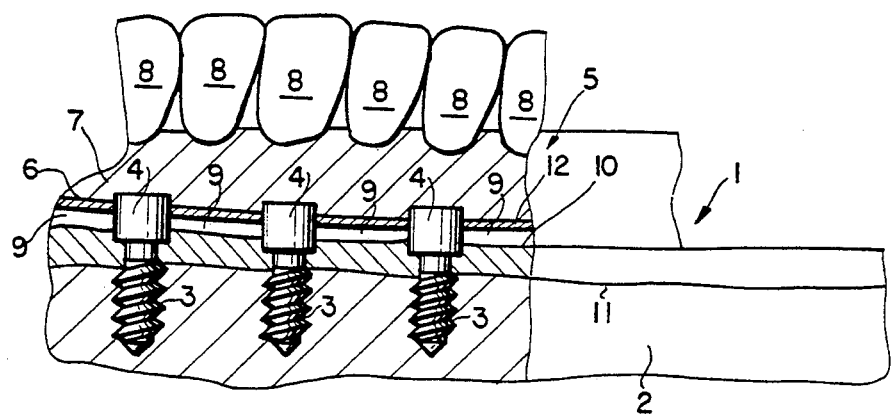
FIG. 1 is an elevational view diagrammatically illustrating the anchoring of a dental implant in the bone tissue of a patient.
Figure 2:
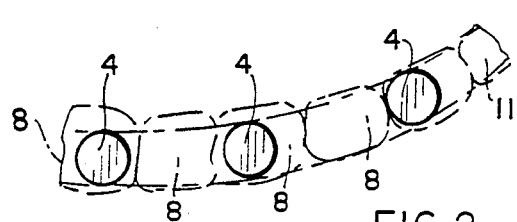
FIG. 2 is a top plan view of the implant in FIG. 1.

Referring to FIGS. 1 and 2, therein is shown a dental implant 1 secured to the bone tissue 2 of a jaw of a patient. While the drawing is directed to the placement of an implant 1 into the lower jaw, it is equally possible to achieve implantation in the upper jaw of the patient.

The implant 1 comprises a root fixture 3 which is made of titanium and which is screwed into a precisely drilled hole in the bone tissue 2 or otherwise affixed in conventional manner. By virtue of the construction of the implant of titanium, it becomes integrated with the bone tissue by a phenomenon known as "osseointegration". Secured to each fixture is an abutment member 4, for example, by screwing the abutment member 4 into the fixture 3. Other means of attachment are also known but this is not germane to the invention and requires no further elaboration. As evident from FIG. 1 and 2, the root fixtures and abutment members are spaced along the jaw. The abutment members 4 are adapted to be secured with a prosthesis 5. The prosthesis comprises an attachment portion 6 affixed to the abutment members 4, a gingival simulating portion 7 and teeth 8. The prosthesis can be an entire upper or lower jaw prosthesis or it can be divided into quadrants. It is also possible to mount each tooth as a separate prosthesis on an individual abutment member. In all of these arrangements, a clear space 9 is formed between surface 10 of the gum 11 of the patient and the confronting surface 12 of the prosthesis 5.

In order to achieve proper oral hygiene of the implant 1, the prosthesis 5, and adjacent teeth, it is essential to effect proper plaque removal from all exposed surfaces. Generally, the facial surfaces of the implant and prosthesis are readily cleaned by conventional or modified toothbrushes. However, the lingual or posterior surfaces of the abutment members are not accessible to toothbrush control and represent a serious site for build-up of bacterial plaque. The importance of sound hygiene measures for implant maintenance is of great significance and the recent 1988 National Institutes of Health Consensus Development Conference recommended that a patient's inability to accomplish adequate oral hygiene be considered a contraindication to implant placement.

The inaccessibility of the lingual surfaces of the abutment members makes these particular breeding points for bacterial plaque in view of their relative inaccessibility. Primarily, this is due to the obscuring of the abutment members by the substructure of the prosthesis which interferes with normal hygiene procedures. The conventional use of floss, ribbon or other similar flexible cleaning materials is difficult since it is hard to insert the cleaning material between the abutment members and then wrap it around the lingual surface and project it at the facial side where it can be engaged by the fingers of the user.

Figure 3:
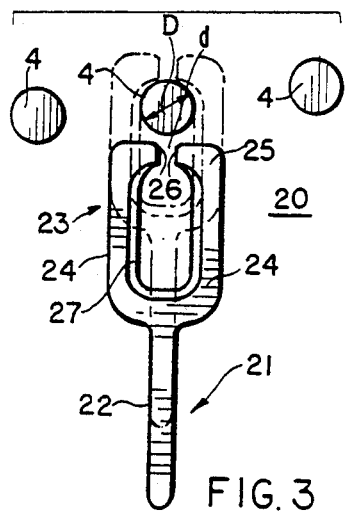
FIG. 3 is a plan view showing a first embodiment of the invention in association with the abutment members of the implant.

FIG. 3 shows a first embodiment of the invention which makes possible cleaning of the surfaces of the abutment members, especially the lingual surfaces, in a simple manner. Therein is shown a cleaning device 20 which comprises a support member 21 having a relatively rigid handle 22 and an operative portion 23 on and extending from handle 22. The support member 21 is made of a thermoplastic material such as nylon and it can be formed with an inner reinforcing metal body. The thermoplastic material of the support member 21 provides the support member with sufficient flexibility so that it can deform slightly when force is applied thereto and return to its initial shape when the force is removed. The outer surface of the support member can be coated with Teflon or the entire body of the support member 21 can be made of Teflon. The operative portion 23 comprises a holder in the form of an elongated loop of flat, band-like configuration with two arms 24 having curved ends 25 constituting deviating portions with surfaces 26 facing one another and spaced apart by a distance d to form a gap which is less than the transverse extent or diameter D of an abutment member 4. The flat inner surface of the arms 24 is covered by a lining formed as a layer of cleaning material 27 which can be in the form of bristles, sponge, cotton, fabric or floss.

In order to effect cleaning of the lingual surfaces of the abutment members, the ends 25 of the cleaning device 20 are brought into contact with the facial surface of an abutment member and are pressed against the abutment member to displace the deviated portions 25 away from one another so that the abutment member 4 will enter into the clear space between the arms 24. The deviated portions 25 will now be positioned behind the abutment member 4 in confronting relation with the lingual surface of the abutment member as shown in dotted outline in FIG. 3. By effecting a rotary oscillating and up and down motion of the cleaning device 20 through engagement of the handle 22, the cleaning material 27, braced by the holder, will clean the entire surface of the abutment member 4 including the lingual surface, the buccal surface, and the proximal surfaces.

Figure 4:
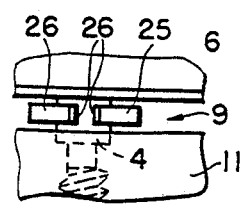
FIG. 4 is an end view from the lingual side of the device and abutment member of FIG. 3.
Figure 5:
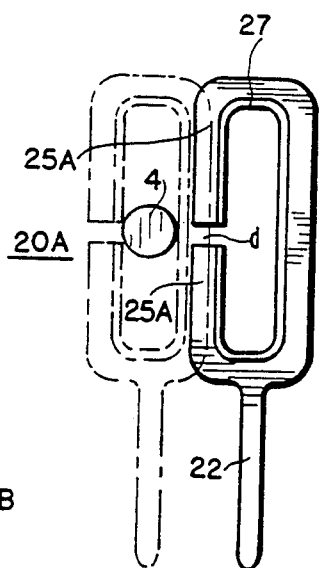
FIG. 5 shows another embodiment of the cleaning device.

FIGS. 5 shows an embodiment similar to that in FIGS. 3 and 4 and therein the cleaning device 20A has the space d formed in the middle of one of the side arms of the holder rather than at the ends of the arms. Cleaning is effected by inserting the entire device 20A between adjacent abutment members (temporarily deforming the device, if necessary) until the space d is in confronting relation with a proximal surface of abutment member 4. The device 20A is then displaced laterally so that the deviated portions 25A will engage around the abutment member 4 as shown in dotted outline in FIG. 5. In this position, the lingual surface of the abutment member can be cleaned by pulling the handle 22 in a direction away from the abutment member and then moving the cleaning device 20a up and down. In order to clean the facial surface of the abutment member, the handle 22 is pushed in a direction into the mouth so that the facial surface will now come into contact with the cleaning layer 27 on the inner surface of the cleaning device 20A. At the same time that the lingual and facial surfaces are being cleaned, the proximal surfaces will be cleaned as well.

Figure 6:
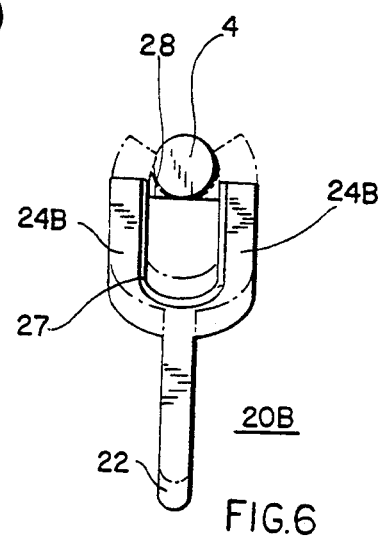
FIG. 6 shows a further embodiment of the cleaning device.
Figure 7:
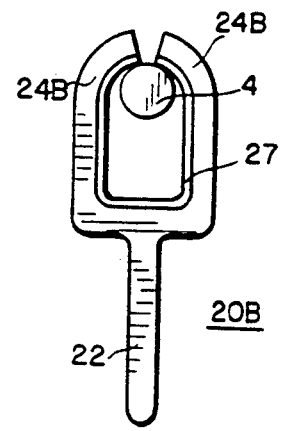
FIG. 7 shows the device of FIG. 6 in an operative stage.

FIGS. 6 and 7 show a further embodiment 20B of the cleaning device which is similar to that in FIGS. 3 and 4 except that the arms 24B of the cleaning device 20B are spaced apart by a distance which is greater than the diameter of the abutment member 4 and a flexible tensioning element 28 is tautly connected to the arms 24B at the ends thereof. When the cleaning device 20B is pressed inwardly into the mouth so that the tensioning element 28 bears against the abutment member 4, continued pressure will cause the tensioning element 28 to be stretched and to apply tensile force to the arms 24B so that these arms will deform and encircle the abutment member 4 as shown in FIG. 7. In this deformed condition, a combined rocking and up and down motion of the cleaning device 20B will achieve cleaning of the entire lingual surface of the abutment member.

Figure 8:
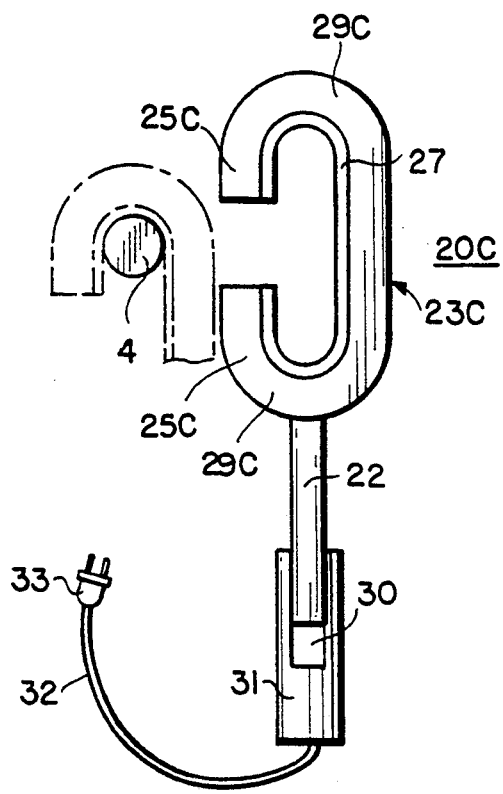
FIG. 8 shows a further embodiment of the device.

FIG. 8 shows an embodiment 20C of the cleaning device which is similar to the embodiment shown in FIG. 5, except that the distance between the arms 25C is greater than the diameter of the abutment member 4. In this way, it is not necessary for the arms to be deformed t permit the abutment member 4 to enter into the interior of the operative portion 23C and become engaged with the cleaning element 27. It then becomes sufficient merely to insert the cleaning device 20C between adjacent abutment members and engage the rounded hook portions 29C with the abutment member in the manner as shown in the dotted outline in FIG. 8. In this way, the lingual, facial, and proximal surfaces of the abutment member can be readily cleaned. In addition, a vibrating device 30 is fixed in a gripping element 31 which fits onto handle 22 so that the vibrating device 30 will be in contact with the handle 22. An electrical line 32 is connected by a plug 33 to a power source (not shown) whereby the cleaning device 20C will be subjected to rapid vibration to assist in the cleaning of the surfaces of the abutment member 4.

Figure 9:
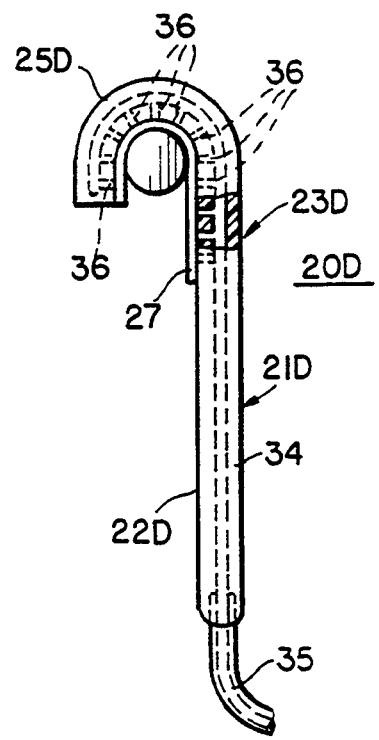
FIG. 9 shows yet another embodiment of the device.

FIG. 9 shows another embodiment 20D of the cleaning device and herein the support member 21D is of inverted "J" shape and it has a single deviated portion 25D at its end extending integrally from the straight handle 22D. The cleaning material 27 is affixed to an interior surface of the operative portion 23D. The support member 21D is provided with an internal channel 34 which is connected by a tube 35 to a water irrigation source (not shown). A series of apertures 36 are formed in the operative portion 21D and extend from the channel 34 to openings in the inner surface leading to the cleaning material 27. The cleaning device 20D is used in a manner similar to that in FIG. 8 in that the operative portion is inserted between adjacent abutment members so that the deviated portion 25D engages the abutment member 4 at its lingual surface. By moving the operative portion up and down and with slight rocking movement, the lingual, proximal and facial surfaces of the abutment member will be cleaned. In addition, the connection of tube 35 to the irrigation source will cause jets of water to penetrate the cleaning material and be ejected with force against the surface of the abutment member to assist in the cleaning thereof.

Figure 10:
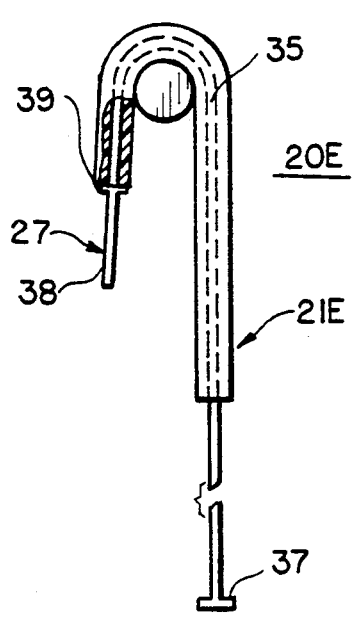
FIG. 10 shows still another embodiment of the device, partly broken away and in section, in an initial position around an abutment member.

FIG. 10 shows another embodiment 20E of the cleaning device and this embodiment comprises an operative portion 21E of inverted "J" shape similar to that in FIG. 9. Instead of channel 34 being a water channel, the cleaning device 20E is provided with a channel 35 in which the cleaning element 27 is freely and slidably engaged. The cleaning element can be floss or fabric but preferably is a ribbon or Super Floss (a trademark of Oral-B, Redwood City, Calif.).

The cleaning element 27 which is freely slidable in channel 35 in the cleaning device 20E is provided with fixed stops or abutment members 37 and 39 to restrict its free sliding movement. In particular, as seen in FIG. 10, the cleaning element 27 has a free end 38 which projects from the end of the cleaning device 20E when the abutment member 39 abuts against the end of the cleaning device 20E. At its other end, a substantial length of the cleaning element 27 extends from the cleaning device 20E and the abutment member 37 is placed at the end of the cleaning element remote from the cleaning device 20E. The free end 38 of the cleaning element 27 is stiff and shape retentive. In use, the cleaning device 20E is inserted between adjacent abutment members in the same manner as in the embodiment of FIG. 9. Upon such insertion, the free end 38 will now project facially where it can be engaged by the user. The cleaning device 21E can now be manipulated to slide on the cleaning element 27 so that it can be removed from the mouth of the user in the manner shown in FIG. 11. In this condition, the cleaning element 27 can now be wrapped around the lingual surface of the abutment member 4 and crisscrossed at the facial surface of the abutment member whereupon the cleaning element 27 can be utilized to clean the entire surface of the abutment member with a conventional back and forth "shoe shine" motion.

Figure 11:
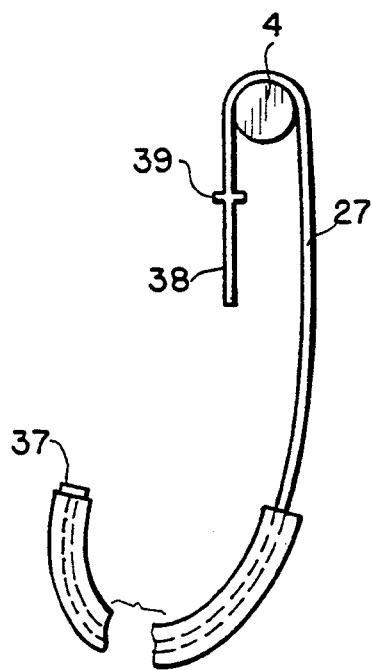
FIG. 11 shows a cleaning position of the device in FIG. 10 in which the cleaning element is operatively engaged around the abutment member.

In the embodiments in FIGS. 1–9, the cleaning element 27 is affixed to the cleaning device itself and the cleaning of the abutment member takes place by engaging the handle of the cleaning device and manipulating the cleaning device with a rocking, reciprocating motion. In the embodiment of FIGS. 10 and 11, the operative portion of the cleaning device serves to position the cleaning element 27 around the lingual surface of the abutment member and after such positioning the operative portion is removed and the cleaning element itself achieves the cleaning.

Although the invention has been described in relation to specific embodiments thereof, it will become apparent to those skilled in the art that numerous modifications and variations can be made within the scope and spirit of the invention as defined in the attached claims.

What is claimed is:

1. A dental cleaning device comprising a support member including a relatively rigid handle and an operative portion on and extending from said handle, said operative portion being constituted and shaped for penetrating between spaced adjacent abutment members of dental implants and including a deviated portion to confront a lingual surface of one of said abutment members when the operative portion is inserted between said abutment members, and cleaning means having a flexibility greater than that of said support member and operatively associated with said operative portion to engage said one abutment member over at least said lingual surface thereof to clean the same, said operative portion comprising a holder made of relatively rigid plastic material, said holder being in the form of an elongated loop of flat band-like configuration having a flat inner surface, said holder having a gap therein through which an abutment can pass by flexible deformation of said holder, said cleaning means comprising a lining of cleaning material covering said flat inner surface of said holder to face inwards in said loop and be braced by said holder for cleaning the surface of said abutment.

2. A dental cleaning device as claimed in claim 1 wherein said plastic material enables said holder to change its shape and increase the size of said gap when force is applied thereto and to return to its original shape when said force is removed.

3. A dental cleaning device as claimed in claim 2 wherein said loop comprises a yoke on said handle having opposed arms with one said deviated portion on each arm, the deviated portions facing one another to form said gap and being spaced apart by a distance less than a transverse extent of said abutment member, said arms and deviated portions being flexible to enable the abutment member to be inserted between the deviated portions and engaged between said arms by elastically forcing the arms apart.

4. A dental cleaning device as claimed in claim 1, wherein said deviated portion comprises a rounded portion at one end of said loop.

5. A dental cleaning device as claimed in claim 4 wherein said rounded portion ha a hook shape for engaging around the lingual surface of said one abutment member.

6. A dental cleaning device as claimed in claim 4 wherein said loop is of C-shape with opposed rounded portions of hook shape, one facing the lingual surface of said one abutment member, the other facing a facial surface of said one abutment member.

7. A dental cleaning device as claimed in claim 1 comprising means for vibrating said support member.

8. A dental cleaning device as claimed in claim 1 comprising irrigation means for passing an irrigation fluid through said support member and against said abutment member.

9. A dental cleaning device as claimed in claim 1, wherein said loop has flat side arms and opposed curved end portions, said gap being in one of said end portions, said handle being connected to the other of said end portions.

10. A dental cleaning device as claimed in claim 1, wherein said loop has flat side arms and opposed curved end portions, said gap being in one of said side arms to define a C-shape for said loop.

11. A dental cleaning device for cleaning spaced abutment members of a dental implant comprising a flexible cleaning element constructed of material capable of cleaning the surface of an abutment member by rubbing the cleaning element against said surface of the abutment member, and a relatively rigid hand-held support means slidably receiving said flexible cleaning element such that the cleaning element has free ends extending from opposite ends of said support means, said support means being shaped to serve as a guide means for positioning the cleaning element at a lingual surface of the abutment member with the free ends of the flexible cleaning element projecting in front of a facial surface of the abutment member so that after removal of the support means from the abutment member, the abutment member can be cleaning by crisscrossing the cleaning element on the abutment member and moving the cleaning element back and forth on the abutment member.

12. A method of cleaning the surfaces of spaced adjacent abutment members of a dental implant comprising engaging from the facial side of an abutment member of a dental implant, a relatively rigid support member so that a hook portion of the support member faces the lingual surface of said abutment member, providing a flexible ribbon which passes freely through the support member so that when the hook portion faces the lingual surface of said abutment member a first free end portion of the ribbon projects from said hook portion at one side of the abutment member and a second free end portion of the ribbon projects from said support member at an opposite side of said abutment member, withdrawing the support member from behind the abutment member to leave the ribbon encircling the lingual surface of the abutment member and projecting forwardly at both sides of the abutment member, and cleaning the abutment member by moving the ribbon on said abutment member.

13. A method as claimed in claim 12 comprising fixing the cleaning material as a layer on the support member.

14. A method as claimed in claim 13 wherein said support member is formed of resilient material which is shape-retaining but flexible, said hook portion of the support member being formed by elastically deforming the support member.

15. A dental cleaning device comprising a support member including a relatively rigid handle and an operative portion on and extending from said handle, said operative portion being constituted and shaped for penetrating between spaced adjacent abutment members of dental implants and confronting a lingual surface of one of said abutment members, and cleaning means having flexibility greater than that of said support member and operatively associated with said operative portion to engage said one abutment member over at least said lingual surface thereof to clean the same, said operative portion comprising a yoke on said handle having opposed arms spaced apart by a distance greater than a transverse extent of said abutment member, and a flexible tensioning element connected to and tautly extending between said arms to cause said arms to deform and encircle the lingual surface of said abutment member when the abutment member is urged against said flexible element and between said opposed arms.

16. A dental cleaning device as claimed in claim 15 wherein said cleaning means includes a layer of cleaning material affixed to said operative portion and extending therealong for cleaning said abutment member upon movement of the operative portion around the abutment member.

17. A dental cleaning device comprising a support member including a relatively rigid handle and an operative portion on and extending from said handle, said operative portion being constituted and shaped for penetrating between spaced adjacent abutment members of dental implants and including a deviated portion to confront a lingual surface of one of said abutment members when the operative portion is inserted between said abutment members, and cleaning means having a flexibility greater than that of said support member and operatively associated with said operative portion to engage said one abutment member over at least said lingual surface thereof to clean the same, said support member being hollow, said cleaning means comprising a flexible cleaning element extending through said support member in freely sliding fashion, said flexible cleaning element extending from said support member at opposite ends thereof, and stop means on said flexible cleaning element outside one of said ends of the support member for limiting relative sliding movement of the cleaning element and the support member.

18. A dental cleaning device as claimed in claim 17, wherein said deviated portion comprises a rounded portion on said support member, said cleaning element includes an end portion extending from and beyond said rounded portion of the support member, said end portion being relatively stiff to maintain its shape.

19. A dental cleaning device as claimed in claim 18 wherein said cleaning element comprises a ribbon.

* * * * *